(12) United States Patent
Riley et al.

(10) Patent No.: US 7,601,312 B2
(45) Date of Patent: Oct. 13, 2009

(54) MEDICAL INSTRUMENT RETAINER ASSEMBLY

(75) Inventors: Edward D. Riley, Falmouth, ME (US); Gerald B. Kern, Westminister, CA (US); Horst Chr. Weiss, Muehlheim (DE)

(73) Assignee: Riley Medical, Inc., Auburn, ME (US)

( * ) Notice: Subject to any disclaimer, the term of this patent is extended or adjusted under 35 U.S.C. 154(b) by 572 days.

(21) Appl. No.: 11/177,541

(22) Filed: Jul. 8, 2005

(65) Prior Publication Data

US 2007/0009408 A1    Jan. 11, 2007

(51) Int. Cl.
*A61L 2/00* (2006.01)
(52) U.S. Cl. ............... 422/300; 248/684; 248/309.1
(58) Field of Classification Search ........... 248/684, 248/309.1, 309.2; 422/297, 300
See application file for complete search history.

(56) References Cited

U.S. PATENT DOCUMENTS

| | | | | |
|---|---|---|---|---|
| 3,255,987 | A * | 6/1966 | Gatch | 248/220.31 |
| 4,262,799 | A * | 4/1981 | Perrett | 206/363 |
| 4,798,292 | A | 1/1989 | Hauze | |
| 5,211,915 | A | 5/1993 | Mönch | |
| 5,407,069 | A | 4/1995 | Schmieding et al. | |
| 5,424,048 | A | 6/1995 | Riley | |
| 5,433,930 | A * | 7/1995 | Taschner | 422/300 |
| 5,467,874 | A * | 11/1995 | Whitaker | 206/378 |
| 5,525,314 | A * | 6/1996 | Hurson | 422/300 |
| 5,681,539 | A | 10/1997 | Riley | |
| 5,759,502 | A | 6/1998 | Spencer | |
| 5,785,218 | A * | 7/1998 | LaLone et al. | 224/42.24 |
| 5,827,487 | A | 10/1998 | Holmes | |
| 6,193,932 | B1 | 2/2001 | Wu et al. | |
| 6,244,447 | B1 * | 6/2001 | Frieze et al. | 211/85.13 |
| 6,331,280 | B1 | 12/2001 | Wood | |
| 6,436,357 | B1 * | 8/2002 | Frieze et al. | 422/300 |
| 6,969,498 | B1 * | 11/2005 | Riley | 422/300 |
| 6,991,414 | B1 * | 1/2006 | Mensah | 411/231 |

FOREIGN PATENT DOCUMENTS

DE    19819328 A1    11/1999

* cited by examiner

*Primary Examiner*—J. Allen Shriver, II
*Assistant Examiner*—Steven M Marsh
(74) *Attorney, Agent, or Firm*—Hayes Soloway P.C.

(57) ABSTRACT

A retainer assembly for locating a medical device in a container having a wall with a vent hole. The retainer assembly includes a retainer with an undersurface that is larger than the vent hole and an axial passage having a selected length and cross section extending into the retainer from the surface. The assembly also includes a keeper having a head that is larger than the vent hole and a sleeve extending from the head to an end. The sleeve has substantially the same cross-section as the passage and is shorter axially than the passage so that when the retainer surface is engaged to one face of the container wall so that the passage is aligned with the vent hole and the keeper is engaged to the retainer by frictionally engaging its sleeve in the passage until its head contacts the opposite face of the container wall, the retainer becomes securely, but releasably, anchored to the container wall.

9 Claims, 1 Drawing Sheet

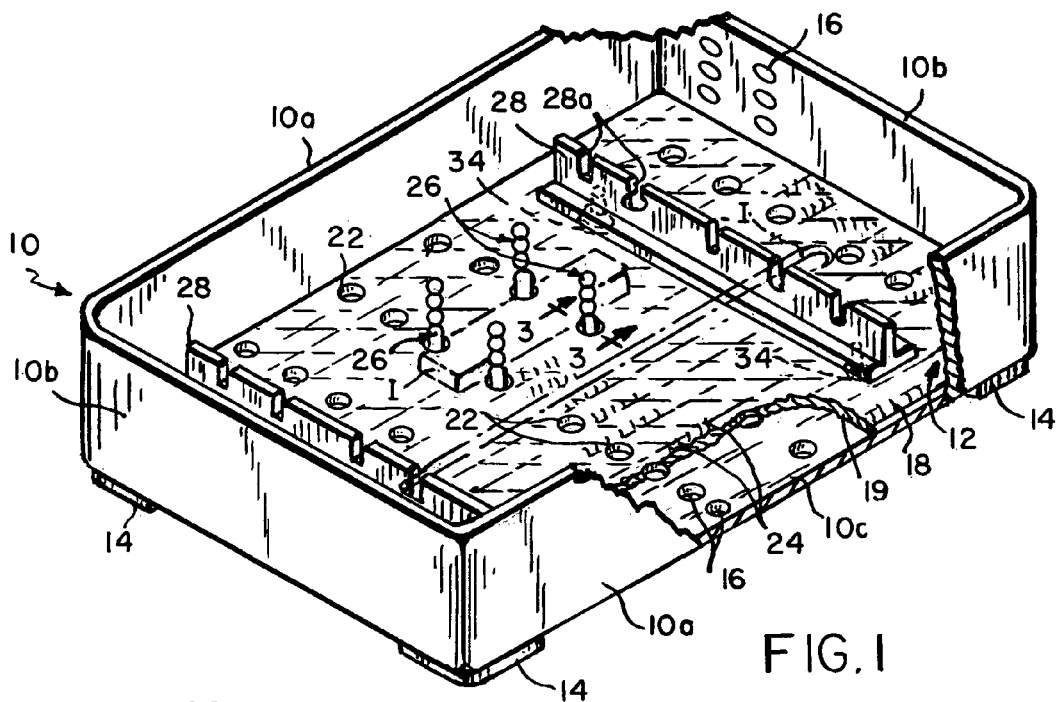
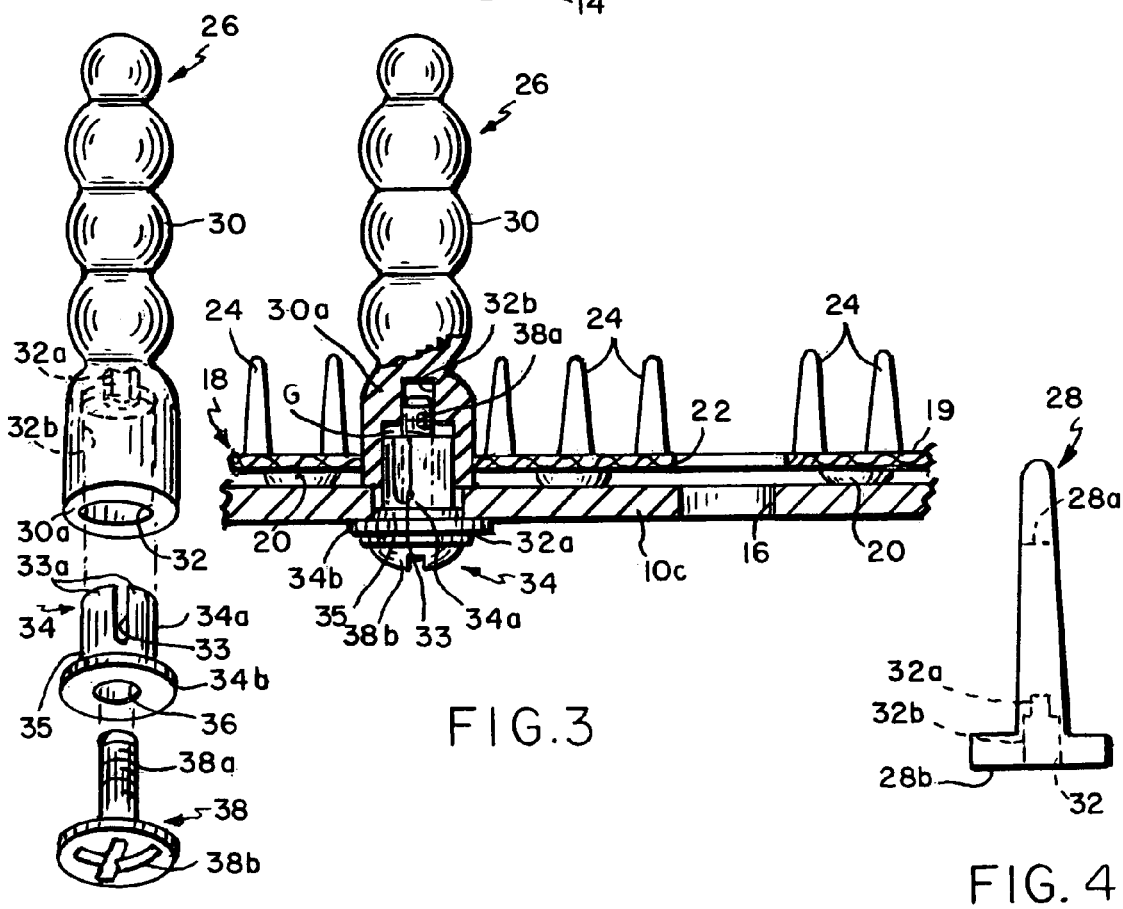

MEDICAL INSTRUMENT RETAINER ASSEMBLY

BACKGROUND OF THE INVENTION

This invention relates to a retainer assembly for retaining medical instruments. It relates especially to a retainer assembly capable of holding irregularly shaped medical instruments at fixed positions in a tray or other container.

There exists in the prior art various retainers and accessories for fixing the positions of articles of one kind or another. These include hooks, pegs, clips, brackets, etc. Such retainers may be used in a wide variety of different applications. For example, they are commonly used in the medical field to fix the positions of various surgical instruments, devices and prostheses while those articles are being transported and processed in one way or another. Accordingly, we will describe the invention in that context. It should be understood, however, that the present invention has application in other fields besides the medical field.

Medical instruments are often transported in trays. Prior to use, such instruments are placed in a tray and subjected to sterilization. To improve the circulation of steam throughout the tray, the tray bottom wall and perhaps the tray side walls are usually formed with a multiplicity of vent holes. In order to maintain a separation between the various instruments in the tray, the instruments are supported or retained by posts, brackets or other retainers anchored to the tray. Following sterilization, the tray full of instruments may be transported to an operating room and placed close to a surgical team whose members may withdraw the instruments from the tray as needed for the particular surgical procedure being performed. Usually, the instruments are selectively arranged or organized in the tray so that they can be picked from the tray in the order in which they are needed for the particular procedure. Examples of such trays are disclosed in my U.S. Pat. Nos. 5,424,048 and 5,681,539.

The known retainers or accessories for positioning instruments in a tray include a simple post or a blade-like bracket which is releasably secured to the bottom wall of the tray at a selected location thereon. The bracket usually has slots, openings, fingers, etc., which are adapted to receive or engage medical instruments so that the bracket can support and/or fixate the instruments within the tray. Often the post or bracket is adjustably anchored to the bottom wall by utilizing selected vent holes in that wall. In other words, the retainer is formed with fastening means which may be inserted into a selected vent hole or holes in the bottom wall of the tray and secured to the bottom wall around the hole(s).

The fastening means on the post or bracket may be one or more passages for receiving threaded fastener(s) inserted through the selected vent hole(s) from the underside of the tray. Alternatively, the fastening means may be a reduced diameter neck or necks extending down from the underside of the post or bracket and which is/are dimensioned and arranged so that each neck can be received in a vent hole in the bottom wall of the tray and releasably anchored to the bottom wall, e.g. by a C-clip clipped around the neck segment that projects below the bottom wall. In some constructions, each neck is terminated by a barb which may snap into the associated vent hole in the tray bottom wall to anchor the retainer(s).

In any event, by properly positioning two or more retainers in the tray, those fixtures can engage and fixate the opposite ends of different length medical instruments.

While such conventional retainers and accessories are satisfactory for many applications, they do have certain drawbacks. More particularly, when making up a tray of medical instruments for a particular operation, the usual procedure is to lay down the various instruments at selected locations in the tray. Then, the posts, brackets, and other accessories are positioned around the instruments so as to "corral" or support them at those locations. Then, the accessories are anchored to the tray bottom wall at the closest vent hole(s) therein. Thus, when threaded fasteners are used to anchor the retainers to the tray bottom wall, the tray has to be upended or overturned in order to turn down the fasteners with a screwdriver or the like. This is an annoyance and an inconvenience to healthcare personnel who are usually pressed for time. Those retainers with barbs which snap into the vent holes in the bottom of the tray usually acquire a loose fit over time. This is because the barbs that plug into the vent holes become worn away by the sharp edges of those holes. Resultantly, the retainers can become separated from the tray during routine handling of the tray thereby upsetting the organization of the medical instruments in that tray.

Another problem with the retainers which snap into place as aforesaid is that they are dimensioned to fit in a tray having a specific wall thickness. The same holds true for accessories retained by C-clips which snap into grooves in the retainer necks as described above. In reality, the wall thickness of medical trays can differ depending upon the tray material. For example, an aluminum tray may have a wall thickness of 2 mm., a stainless steel tray may have a thickness of 1 mm., and a plastic tray may have a wall thickness of 3 mm. It is impractical to stock three different sets of retainers of the last-mentioned type that will reliably and securely anchor to trays made of such different materials.

Therefore, there is a need to provide medical instrument retainers or accessories that can be anchored reliably to most if not all of the vented medical instrument trays and containers in use today with minimum inconvenience.

SUMMARY OF THE INVENTION

Accordingly it is an object of the invention to provide a retainer assembly for retaining medical instruments in a sterilization tray or similar container.

Another object of the invention is to provide an assembly of this type which can accommodate trays having various different wall thicknesses.

A further object of the invention is to provide such an assembly which can be anchored to the tray without having to overturn the tray.

Still another object of the invention is to provide a retainer assembly which can be installed in a tray without the user having a direct view of all of the components of the assembly.

Still another object of the invention is to provide such as assembly which will remain firmly anchored to the tray despite rough and prolonged handling of the tray.

A further object of the invention is to provide a retainer assembly of this type which can withstand repeated attachments to and detachments from the tray without suffering excessive wear as could weaken future attachments to the tray.

Still another object of the invention is to provide a retainer assembly having all of the above advantages yet whose cost is comparable to conventional retainer assemblies of this general type.

Briefly, my retainer assembly is especially designed for use with a medical instrument tray having columns and rows of vent holes in the bottom wall of the tray through which steam or other fluid may circulate when instruments in the tray are being sterilized. These holes also serve as anchoring points for the various retainers or accessories to be described that fixate instruments within the tray.

Very often a sterilization tray will contain a so-called finger mat which rests on the bottom wall of the tray. As the name implies, the mat includes a multiplicity of upstanding resilient fingers. When medical instruments or the like are placed in the tray so that they rest on the mat, the fingers cushion, and help to fix the positions of, those instruments. The finger mat is usually provided with bumps at its underside to space the base of the mat above the tray wall and with holes which line up with the vent holes in the tray wall so that the mat does not interfere with the circulation of sterilent throughout the tray.

In accordance with the present invention, my retainer assembly includes a retainer such as a post or bracket and at least one keeper in the form of a flanged or headed sleeve or shank. The retainer has an undersurface whose area is larger than that of each vent hole in the tray and at least one passage which extends into the retainer from that undersurface. The lower end segment of each passage is counterbored to receive the sleeve or shank portion of the keeper so that the keeper is held in place within the counterbore by friction. Preferably, the keeper has an axial through hole to provide clearance for a threaded fastener which may be screwed into a threaded segment of the passage in the retainer after the keeper is engaged to the retainer.

In use, a nurse, after organizing the medical instruments in the tray, may position each retainer or accessory at a desired location in the tray so that each passage therein is aligned with an underlying vent hole in the bottom wall of the tray. Then he/she may reach under the tray and press the sleeve portion of a keeper through each of those vent holes from below and into the counterbore of the overlying retainer. The counterbore(s) in the retainer is/are longer than the keeper sleeve(s) such that the assembly can accommodate a relatively wide variation in the wall thickness of the tray. In other words, each keeper can be pushed into its counterbore to a greater or lesser degree depending upon that wall thickness. Preferably also, the keeper sleeve is formed with a step or shoulder adjacent the keeper head so that it tends to center itself in the associated vent hole in the tray wall. When the keeper is pressed home, it is firmly held in place by friction and thus holds the associated retainer in a fixed position in the tray. If the user wishes to reposition a retainer, he/she merely pulls upward on the retainer with sufficient force and each keeper will automatically pull out of the associated counterbore thereby releasing the retainer from the tray. Once the assembler is satisfied with the particular retainer configuration, he/she may, if desired, turn the tray over and install a threaded fastener through each keeper to permanently anchor the retainers to the tray.

BRIEF DESCRIPTION OF THE DRAWINGS

For a fuller understanding of the nature and the objects of the invention, reference should be made to the following detailed description taken in connection with the accompanying drawings, in which:

FIG. 1 is an isometric view with parts broken away showing a medical instrument tray incorporating instrument retainer assemblies according to my invention;

FIG. 2 is an exploded isometric view on a much larger scale showing in greater detail the components of one of the assemblies in FIG. 1;

FIG. 3 is a sectional view with parts in elevation taken along line 3-3 in FIG. 2, and FIG. 4 is an end view enlarged of another retainer assembly in the FIG. 1 tray.

DESCRIPTION OF THE PREFERRED EMBODIMENTS

Referring to FIG. 1 of the drawings, my retainer assembly is for use with a rigid, generally box-like case or tray 10 having a pair of mirror-image side walls 10a, a pair of mirror image end walls 10b, and a bottom wall 10c defining a generally rectangular interior space 12. Preferably tray 10 is provided with integral pads or feet 14 at the four corners of the tray so that the tray bottom wall 10c is spaced above a support surface on which the tray is placed. The tray should be made of a material able to withstand sterilization, e.g. polyphenylsulphone or a non-corroding metal such as aluminum, stainless steel and titanium.

Formed in the bottom wall 10c of tray 10 is a multiplicity of vent holes 16 usually arranged in columns and rows to allow for circulation of steam or other sterilizing fluid through the interior space 12. As will be described in more detail shortly, these holes 16 can also function as anchoring points for the retainers and accessories used to locate various medical instruments within tray 10. Of course, the side and/or end walls of the tray can also be provided with such holes 16 as indicated in FIG. 1.

Preferably tray 10 is fitted with a finger mat 18 which overlies substantially the entire bottom wall 10c of the tray. As best seen in FIG. 3, the finger mat includes a flexible base 19 having bosses or pads 20 extending down from the base to space the mat from the tray bottom wall 10c. Also, the base is preferably provided with a multiplicity of vent holes 22 which are aligned with the vent holes 16 in bottom wall 10c. Finally, the finger mat includes a field of resilient fingers 24 extending up from base 19 except at the locations of the vent holes 22 therein.

Referring to FIG. 1, tray 10 is adapted to contain a plurality of variously shaped medical instruments I. In order to fixate those instrument in the tray, assorted retainers or accessories may be employed. These include solitary assemblies 26 as well as elongated assemblies 28 having notches or slots 28a for receiving instruments I. Of course, other retainer shapes and sizes are also contemplated by this invention.

As best seen in FIG. 2, each retainer assembly 26 includes an elongated post 30 which is preferably scalloped along its length to better engage the sides of an instrument I. Post 30 has an undersurface or end 30a whose cross sectional area is larger than that of the vent holes 16 in tray 10. Also post 30 is formed with an axial passage 32 extending up from surface 30a. The upper end segment 32a of that passage has a relatively small diameter and may be threaded. The passage 22 also includes a larger diameter counterbore 32b adjacent surface 30a, the cross section of which is no larger than that of the vent holes 16 in tray 10.

The other component of retainer assembly 26 is a keeper 34 which has a cylindrical sleeve or shank 34a whose diameter is substantially the same of that of counterbore 32 and a flange or head 34b at one end of the sleeve. Preferably the sleeve is slotted at 33 to form resilient tines 33a between the slots and is formed with a shoulder or step 35 adjacent flange 34b as best seen in FIG. 3 which is sized to center the keeper in a vent hole 16 of the tray 10. Preferably also, an axial through hole 36 is formed in the keeper 34 to allow passage of the threaded shaft 38a of a fastener 38 having a head 38b at one end of the shaft.

When the keeper 34 is mated to post 30 so that the keeper sleeve 34a is received in counterbore 32b of the post, the keeper sleeve with its resilient tines 33a will frictionally engage the post. The length and diameter of the shaft 38a of threaded fastener 38 is such that when the keeper 34 is received in counterbore 32b, the fastener 38 may be inserted through hole 36 in the keeper and turned down into the threaded segment 32a of passage 32 in the post as shown in FIG. 3.

Retainer 26 is installed in tray 10 by inserting the post surface 32a through a hole 22 in mat 18 so that surface 32a engages the tray bottom wall 10c around a selected vent hole 16 therein. Preferably, holes 33 are somewhat larger than holes 16 to facilitate that. Then, the assembler reaches under the tray and inserts a keeper 34 through that same vent hole from below the tray so that the keeper sleeve 34a is inserted into the passage counterbore 32a of the overlying post 30. The keeper is pressed into the post until the keeper head 34b engages the underside of bottom wall 10c. The frictional and resilient engagement of the sleeve 34a against the wall of counterbore 32a positively secures the keeper to the post thereby releasably anchoring the post 30 to the tray 10.

As best seen in FIG. 3, the keeper sleeve 34a is longer than counterbore 32a in the post so as to leave a gap G between the free end of the sleeve and the closed end of the counterbore. This gap G accommodates a tray wall 10c having a range of thicknesses. In other words, since the keeper 34 is retained in the post 30 solely by friction, there is no set position of the keeper relative the post to achieve an anchoring of the post to the tray 10. This contrasts sharply with those conventional retainers described at the outset which are anchored by a snap fit or a C-clip whose fastening requires a tray of a given wall thickness.

The retainer assemblies 28 shown in FIG. 1 are anchored to the tray in more or less the same way. More particularly, each retainer 28 has a plurality of passages 32 located along its undersurface 28b to coincide with the positions of the vent holes 16 in tray 10. Keepers 34 may be inserted through the vent holes from below the tray and plugged into the overlying passage counterbores 32b as described above in connection with retainer assemblies 26. Also in the same way, the retainer assemblies 28 may be anchored permanently to the tray by screwing fasteners 38 into the associated passage segments 32a.

Typically a nurse may position medical instruments I in tray 10 in the desired configuration. Then he/she may position retainer assemblies 26, 28 around or under the medical instruments with their passages 32 aligned with the nearest vent holes 16. Then, the nurse may reach under tray 10 and insert keepers 34 through those same vent holes from below the tray so that the keeper sleeves frictionally engage the walls of the corresponding counterbores 32b thereby securing the retainers to the tray. It is important to note that this may be done by feel alone and without having to turn the tray over.

In order to reposition a particular retainer, an upward pull on that retainer with sufficient force will overcome the frictional engagement of the keeper(s) to the retainer allowing those two elements to separate and thereby releasing the retainer from the tray. When the nurse is satisfied with the retainer layout and if that layout is to be longstanding, the nurse may then turn the tray over and install fasteners 38 by inserting them through the holes 36 in the keepers and turning them down into the threaded passage segments 32a of the corresponding retainers.

It will thus be seen that the objects set forth above, among those made apparent from the preceding description, are efficiently attained. Also, certain changes may be made in the above constructions without departing from the scope of the invention. For example, retainers such as shelf or tray brackets may be anchored in the vent holes 16 in the side or end walls of tray 10. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A retainer assembly for locating a medical device in a container, the container having a wall with an opening and a first face and a second face, said retainer assembly comprising
    a retainer including
        a wall surface that is larger than the opening, and
        a first passage extending into the retainer from said surface, said first passage having a selected cross section and a selected length,
    a keeper including,
        a head that is larger than the opening, and
        a hollow shank extending from the head to an end, said shank having substantially the same cross-section as the first passage and being shorter axially than the first passage, wherein the wall surface abuts the first face of the wall of the container and the shank frictionally engages the first passage with the head abutting the second face of the wall of the container.

2. A retainer assembly for locating a medical device in a container, the container having a wall with an opening and a first face and a second face, said retainer assembly comprising
    a retainer including
        a wall surface that is larger than the opening, and
        a passage extending into the retainer from said surface, said passage having a selected cross section and a selected length, and
    a keeper including,
        a head that is larger than the opening, and
        a shank extending from the head to an end, said shank having substantially the same cross-section as the passage and being shorter axially than the passage, wherein the wall surface abuts the first face of the wall of the container, wherein the shank comprises a slotted tube with resilient tines between the slots, and the shank frictionally engages the passage with the head abutting the second face of the wall of the container.

3. A retainer assembly for locating a medical device in a container, the container having a wall with an opening and a first face and a second face, said retainer assembly comprising
    a retainer including
        a wall surface that is larger than the opening, and
        a first passage extending into the retainer from said surface, said passage having a selected cross section and a selected length;
        a threaded passage extension in the retainer, said threaded passage extension having a smaller diameter than the first passage; and
    a keeper including,
        a head that is larger than the opening, and
        a shank extending from the head to an end, said shank having substantially the same cross-section as the passage, wherein the wall surface abuts the first face of the wall of the container, and the shank frictionally engages the passage with the head abutting the second face of the wall of the container.

4. The retainer assembly defined in claim 3 wherein the keeper includes an axial through hole therein.

5. The retainer assembly defined in claim 4 and further including a threaded fastener dimensioned to be inserted through said through hole and threaded into the passage extension.

6. The retainer assembly defined in claim 1 wherein said shank has a radial step adjacent said head.

7. The retainer assembly defined in claim 1 wherein the retainer comprises a post.

8. The retainer assembly defined in claim 1 wherein the retainer comprises a blade-like bracket.

9. The retainer assembly defined in claim 8 and further including a second passage in the retainer similar to the first-mention passage and in spaced parallel relation to the first-mentioned passage.

* * * * *

UNITED STATES PATENT AND TRADEMARK OFFICE
CERTIFICATE OF CORRECTION

| | | |
|---|---|---|
| PATENT NO. | : 7,601,312 B2 | Page 1 of 1 |
| APPLICATION NO. | : 11/177541 | |
| DATED | : October 13, 2009 | |
| INVENTOR(S) | : Riley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 685 days.

Signed and Sealed this

Fifth Day of October, 2010

David J. Kappos
*Director of the United States Patent and Trademark Office*